US010371674B2

(12) United States Patent
Sasaki et al.

(10) Patent No.: US 10,371,674 B2
(45) Date of Patent: Aug. 6, 2019

(54) CHROMATOGRAPH SAMPLER AND METHOD FOR OPERATING CHROMATOGRAPH SAMPLER

(71) Applicant: HORIBA STEC, CO., LTD., Kyoto (JP)

(72) Inventors: Tomohiro Sasaki, Kyoto (JP); Tomotaka Yoshimura, Kyoto (JP); Shoji Narukami, Kyoto (JP); Tsuneaki Maeda, Kyoto (JP)

(73) Assignee: HORIBA STEC, CO., LTD., Kyoto (JP)

(*) Notice: Subject to any disclaimer, the term of this patent is extended or adjusted under 35 U.S.C. 154(b) by 183 days.

(21) Appl. No.: 15/484,396

(22) Filed: Apr. 11, 2017

(65) Prior Publication Data

US 2017/0299556 A1    Oct. 19, 2017

(30) Foreign Application Priority Data

Apr. 13, 2016 (JP) .................... 2016-080657

(51) Int. Cl.
*G01N 30/02* (2006.01)
*G01N 30/16* (2006.01)
*G01N 30/38* (2006.01)

(52) U.S. Cl.
CPC ............ *G01N 30/38* (2013.01); *G01N 30/16* (2013.01); *G01N 2030/025* (2013.01)

(58) Field of Classification Search
CPC ....... G01N 2030/025; G01N 2030/207; G01N 2030/402; G01N 2030/201
See application file for complete search history.

(56) References Cited

U.S. PATENT DOCUMENTS

| 3,923,460 A | * | 12/1975 | Parrott | G01N 30/466 210/264 |
| 4,057,997 A | * | 11/1977 | Chandler | G01N 30/06 73/23.41 |
| 4,837,157 A | * | 6/1989 | Turnell | G01N 30/06 210/198.2 |
| 4,913,821 A | * | 4/1990 | Melcher | G01N 30/88 210/198.2 |
| 4,952,514 A | * | 8/1990 | Haddad | G01N 30/96 210/198.2 |
| 5,049,509 A | * | 9/1991 | Szakasits | G01N 30/40 422/89 |
| 5,468,643 A | * | 11/1995 | Su | G01N 30/16 210/198.2 |

(Continued)

FOREIGN PATENT DOCUMENTS

| JP | 2001343372 A | * | 12/2001 |
| JP | 2015-190875 | | 11/2015 |

*Primary Examiner* — David A Rogers
(74) *Attorney, Agent, or Firm* — Greenblum & Bernstein P.L.C.

(57) ABSTRACT

In order to, in a chromatograph sampler, regulate the pressure of a sample fluid filled in a constant volume tube to be as constant as possible and ensure the reproducibility of measurement, the chromatograph sampler is configured to provide a bypass line between a sample introduction line and a sample discharge line in parallel with the constant volume tube, and when filling the sample fluid in the constant volume tube, flow the sample fluid also through the bypass line in parallel.

8 Claims, 13 Drawing Sheets

(56) References Cited

U.S. PATENT DOCUMENTS

| | | | | |
|---|---|---|---|---|
| 5,965,448 | A * | 10/1999 | Katou | G01N 35/085 |
| | | | | 422/63 |
| 6,474,136 | B1 * | 11/2002 | Nishina | G01N 30/62 |
| | | | | 73/23.42 |
| 6,638,481 | B2 * | 10/2003 | Sklar | G01N 15/1404 |
| | | | | 137/247 |
| 8,436,297 | B2 * | 5/2013 | Jiang | G01N 30/38 |
| | | | | 210/659 |
| 8,944,102 | B1 * | 2/2015 | Wiederin | F16K 11/0743 |
| | | | | 137/625.46 |
| 8,978,444 | B2 * | 3/2015 | Chou | G01N 29/022 |
| | | | | 73/23.42 |
| 9,310,342 | B2 * | 4/2016 | Sakai | G01N 30/24 |
| 10,036,736 | B2 * | 7/2018 | Nichols | G01N 30/20 |
| 2002/0170904 | A1 * | 11/2002 | Rust | F27D 11/00 |
| | | | | 219/385 |
| 2012/0024048 | A1 * | 2/2012 | Maeda | G01N 30/20 |
| | | | | 73/61.55 |
| 2014/0284279 | A1 * | 9/2014 | Warngren | G01N 30/72 |
| | | | | 210/659 |
| 2015/0047730 | A1 * | 2/2015 | Dourdeville | G01N 30/20 |
| | | | | 137/625.47 |
| 2016/0161452 | A1 * | 6/2016 | Tipler | G01N 30/40 |
| | | | | 73/863.21 |
| 2017/0102366 | A1 * | 4/2017 | Tipler | G01N 30/20 |
| 2017/0184553 | A1 * | 6/2017 | Sims | G01N 30/32 |
| 2018/0067068 | A1 * | 3/2018 | Nakama | G01N 30/66 |

* cited by examiner

US 10,371,674 B2

CHROMATOGRAPH SAMPLER AND METHOD FOR OPERATING CHROMATOGRAPH SAMPLER

TECHNICAL FIELD

The present invention relates to a sampler for a sample fluid to be introduced into a chromatograph, and to a method for operating the sampler.

BACKGROUND ART

As this sort of chromatograph sampler, as disclosed in Patent Literature 1, there is one having a mechanism adapted to introduce a constant volume of sample gas into a column.

A specific example of such a chromatograph sampler will be described with reference to FIGS. 1 and 2. This sort of conventional sampler 100 is one including: a constant volume tube 1 having an internal space of constant volume; and a fluid circuit provided on the periphery of the constant volume tube 1, and configured to, after filling a sample gas in the constant volume tube 1, switch the configuration of the fluid circuit, and send out the sample gas filled in the constant volume tube 1 to a column C.

The constant volume tube 1 is a narrow tubular-shaped one having the internal space of constant volume, and formed with a pair of fluid inlet/outlet ports 1a for introducing/leading-out the sample gas.

The fluid circuit includes a carrier introduction line 2, sample introduction line 3, sample discharge line 4, column communicating line 5, and multiport valve 6.

The carrier introduction line 2 is one into which a carrier gas (a gas not reacting with the sample gas and having a peak different from that of the sample gas, such as He, Ar, or $N_2$) is introduced, and the start point thereof is connected to a carrier introduction port 2p communicatively connecting to an unillustrated carrier gas supply source such as a gas cylinder.

In the carrier introduction line 2, a flow rate control device 21 (hereinafter also referred to as a carrier flow rate control device 21) is provided, and it is configured to allow the flow rate of the carrier gas flowing through the carrier introduction line 2 to be controlled constant.

The sample introduction line 3 is one into which the sample gas as a measurement target is introduced, and the start point thereof is connected to a supply port 3p communicatively connecting to an unillustrated sample supply source. The sample supply source is at positive pressure higher than a reference pressure (e.g., atmospheric pressure), but the pressure is not necessarily constant. In the sample introduction line 3, a flow rate limiting member 31 formed of a throttle or a capillary is provided to limit the inflow amount of the sample gas. In addition, as the flow rate limiting member, a flow rate control device may be used.

The sample discharge line 4 is one of which the end point is connected to a discharge port 4p communicatively connecting to an unillustrated discharge space to discharge the sample fluid to the discharge space. The discharge space is kept at a constant pressure (e.g., atmospheric pressure) lower than that of the sample supply source.

The column communicating line 5 is one of which the end point is connected to the column C to send out a fluid flowing therethrough to the column C.

The multiport valve 6 has multiple ports (six here), and is configured to be able to selectively switch the connection mode among the respective ports to any of two modes.

As illustrated in FIGS. 1 and 2, each of the ports is connected with any of the respective inlet/outlet ports 1a of the constant volume tube 1, the end point of the sample introduction line 3, the start point of the sample discharge line 4, the end point of the carrier introduction line 2, and the start point of the column communicating line 5.

Also, it is configured to, when switching the multiport valve 6 to the first mode, as illustrated in FIG. 1, connect one of the fluid inlet/outlet ports 1a of the constant volume tube 1 to the end point of the sample introduction line 3, and connect the other fluid inlet/outlet port 1a of the constant volume tube 1 to the sample discharge line 4.

On the other hand, it is also configured to, when switching the multiport valve 6 to the second mode, as illustrated in FIG. 2, connect the other fluid inlet/outlet port 1a of the constant volume tube 1 to the end point of the carrier introduction line 2, and connect the one fluid inlet/outlet port 1a of the constant volume tube 1 to the column C.

When the sample gas is sent out to the column C for analysis measurement, the multiport valve 6 is kept in the first mode for a predetermined time, then after filling a constant volume of the sample gas in the constant volume tube 1, the multiport valve 6 is switched to the second mode, and the sample fluid in the constant volume tube 1 is pushed out by the carrier fluid controlled to have a constant flow rate and sent out to the column C.

CITATION LIST

Patent Literature

Patent Literature 1: Japanese Unexamined Patent Publication JP-A 2015-190875

SUMMARY OF INVENTION

Technical Problem

However, in such a configuration, every time the sample gas is filled in the constant volume tube 1 in the first mode, the pressure of the sample gas may differ. As a result, the mass (or molar number) of the sample gas sent out to the column C in the subsequent second mode may vary at every time of measurement to prevent the reproducibility of measurement from being ensured.

The reason for this is as follows.

In the first mode, the constant volume tube 1 is connected to the sample supply source through the sample introduction line 3. The pressure of the sample supply source is not necessarily always constant at every time of measurement, and therefore the pressure of the sample gas filled in the constant volume tube 1 also differs at every time of measurement. More strictly speaking, as illustrated in FIG. 3, in the pressure inside the constant volume tube 1, a gradient is generated from the gas inlet port 1a to the gas outlet port 1a, and the gradient varies at every time of measurement.

In that case, as is clear from the gas state equation (pV=nRT), the mass (or molar number) of the sample gas filled in the constant volume tube and sent out to the column varies at every time of measurement even when the sample gas is unchanged, and therefore as described above, a situation where the reproducibility of measurement cannot be ensured occurs.

The present invention is made in consideration of the above-described problem, and a main intended object thereof is to make the pressure of a sample fluid filled in a constant volume tube as constant as possible to ensure the reproducibility of measurement.

Solution to Problem

A chromatograph sampler according to the present invention is one adapted to supply a sample fluid as a measurement target to a column of a chromatograph, and the chromatograph sampler includes:
(1) a constant volume tube (a sample loop) having a pair of fluid inlet/outlet ports;
(2) a sample introduction line into which the sample fluid is introduced from a supply source of the sample fluid;
(3) a sample discharge line (a vent line) from which the sample fluid is discharged to a predetermined discharge space;
(4) a line switching mechanism adapted to switch between a first mode in which any one of the fluid inlet/outlet ports of the constant volume tube is connected to the sample introduction line, the other is connected to the sample discharge line, and the sample fluid is stored in the constant volume tube while circulating, and a second mode in which both of the fluid inlet/outlet ports of the constant volume tube are respectively disconnected from the sample introduction line and the sample discharge line and any one of the fluid inlet/outlet ports is connected to the column;
(5) a control mechanism adapted to keep the line switching mechanism in the first mode to fill the sample fluid in the constant volume tube, and then switch the line switching mechanism to the second mode to introduce the sample fluid in the constant volume tube into the column; and
(6) a bypass line of which one end is connected to the sample introduction line and the other end is connected to the sample discharge line.

In such a configuration, since even when the pressure of the sample supply source varies at every time of measurement, in the first mode in which the sample fluid is filled in the constant volume tube, the constant volume tube and the bypass line are arranged between the sample introduction line and the sample discharge line in parallel, and the sample fluid flows through the constant volume tube and through the bypass line in parallel, the pressure difference between the fluid inlet/outlet ports of the constant volume tube is decreased, and thereby a variation in the pressure of the sample fluid filled in the constant volume tube can be suppressed. For example, by setting the fluid resistance of the bypass line to have a sufficiently small value, the pressure can be regulated to almost the same constant pressure as the pressure of the sample discharge space.

Accordingly, as compared with before, the mass (or molar number) of the sample fluid in the constant volume tube can be kept constant.

Note that the term "connected" here includes not only "direct connected" but also "indirect connected" through a space or flow path (of which the fluid resistance is substantially negligible).

As a result, for example, when the same type of sample fluid is measured multiple times, the sample fluid having a mass that is the same as much as possible at every time of measurement is sent out to the column, and therefore the reproducibility of measurement can be improved.

Specific embodiments include one configured such that: the line switching mechanism is one that in the second mode, connects any one of the fluid inlet/outlet ports of the constant volume tube to a carrier introduction line into which a carrier fluid for transferring the sample fluid is introduced, and connects the other to the column; and in the second mode, the sample fluid in the constant volume tube is pushed out by the carrier fluid and introduced into the column.

In order to shorten the time required to fill the sample fluid in the constant volume tube, it is preferable that the chromatograph sampler further includes an on-off valve provided in the bypass line, and is configured to, in the first mode, flow the sample fluid through the constant volume tube in a state of closing the on-off valve to block the bypass line, and then open the on-off valve to also flow the sample fluid through the bypass line.

In order to more contribute to regulating the pressure inside the constant volume tube to be constant, it is preferable that the chromatograph sampler further includes a flow rate limiting member provided in the sample introduction line and on an upper stream side than the constant volume tube and the bypass line For purposes such as preventing the sample gas from flowing back from the bypass line, it is preferable that the chromatograph sampler further includes
a fluid resistive member provided in the sample discharge line and between the connecting point with the constant volume tube and the connecting point with the bypass line.

Besides utilizing the bypass line, the chromatograph sampler may further include a constant volume mechanism adapted to, at least immediately before switching from the first mode to the second mode, keep the pressure of the constant volume tube at a predetermined value.

Advantageous Effects of Invention

According to the present invention, even when the pressure of the sample supply source varies at every time of measurement, a variation in the pressure of the sample fluid filled in the constant volume tube can be suppressed.

Accordingly, for example, even when the same type of sample fluid is measured multiple times, the sample fluid having a mass that is the same as much as possible at every time of measurement is sent out to the column, and therefore the reproducibility of measurement can be improved.

DESCRIPTION OF EMBODIMENTS

In the following, one embodiment of the present invention will be described with reference to drawings.

Figure 1:
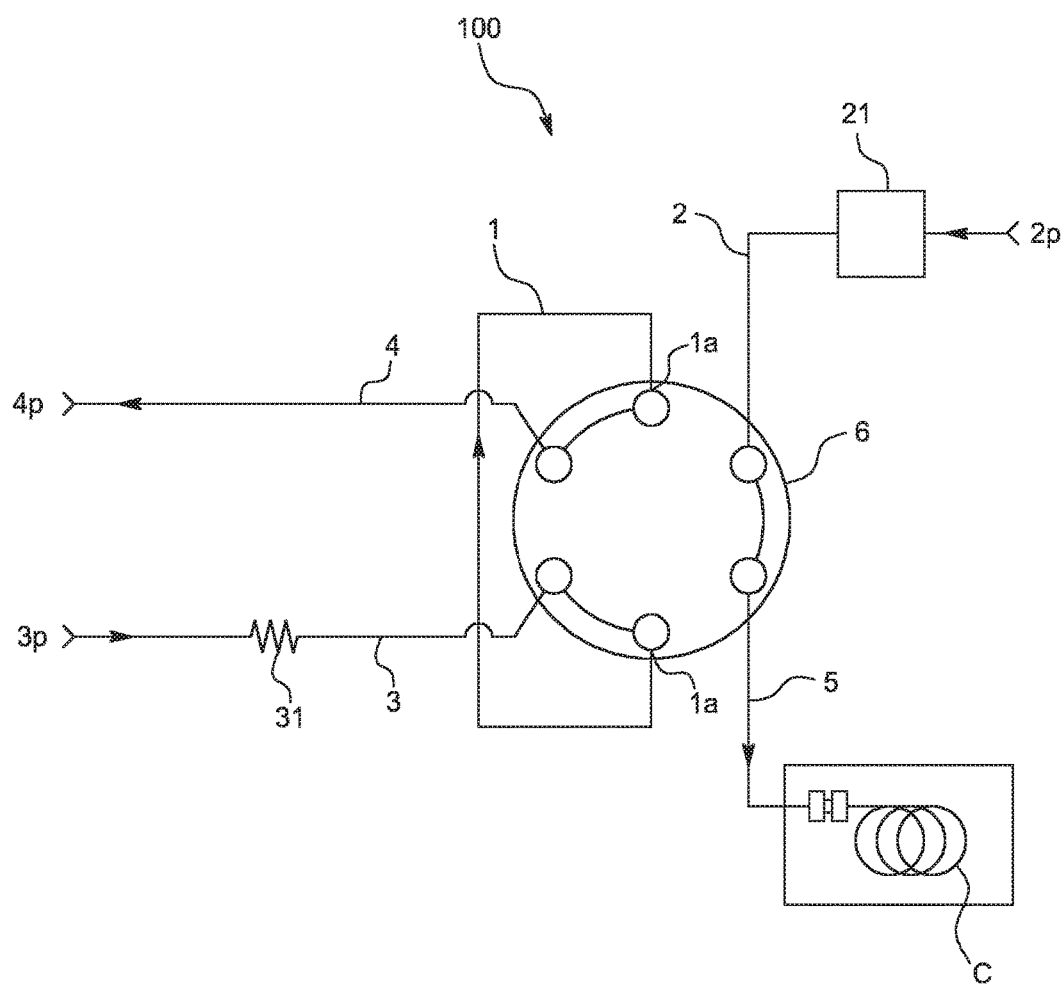
FIG. 1 is a fluid circuit diagram illustrating the configuration and action of a conventional sampler.
Figure 2:
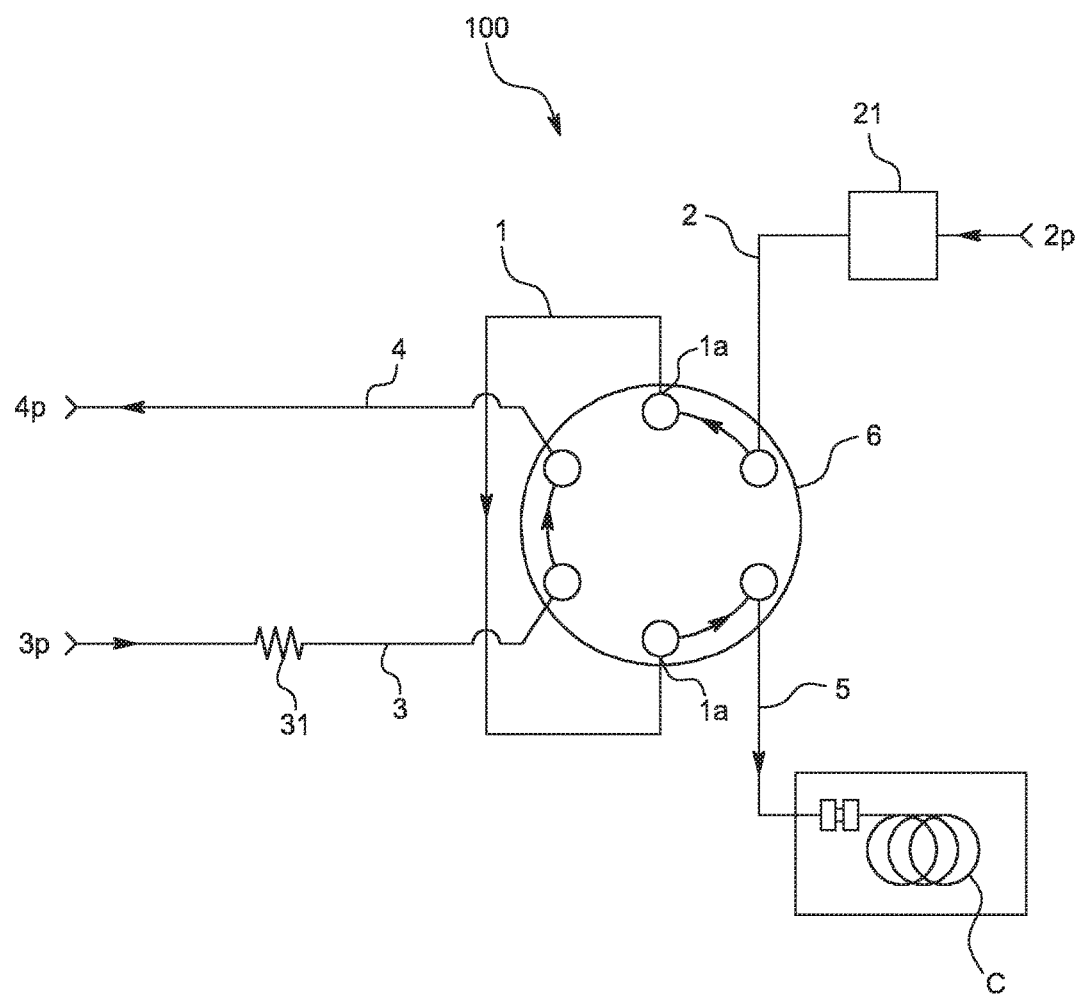
FIG. 2 is a fluid circuit diagram illustrating the configuration and action of the conventional sampler.
Figure 3:
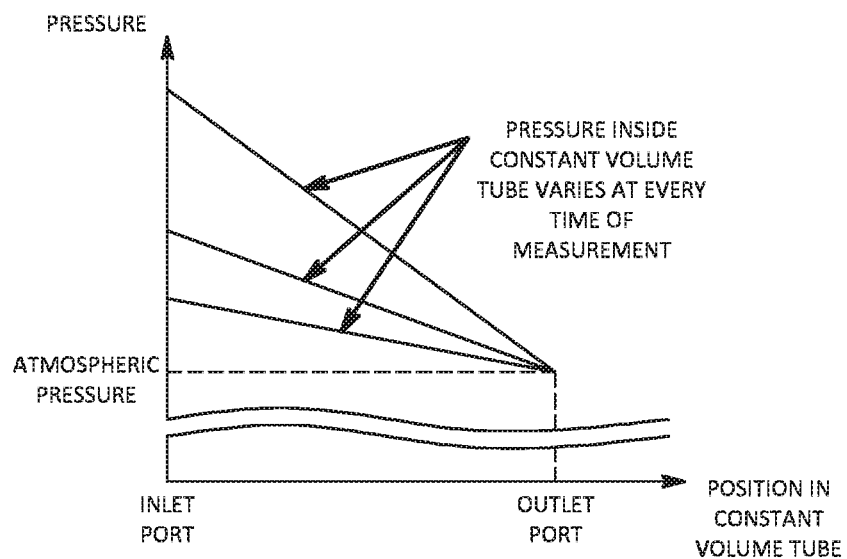
FIG. 3 is a graph illustrating a variation in pressure inside a conventional constant volume tube.
Figure 4:
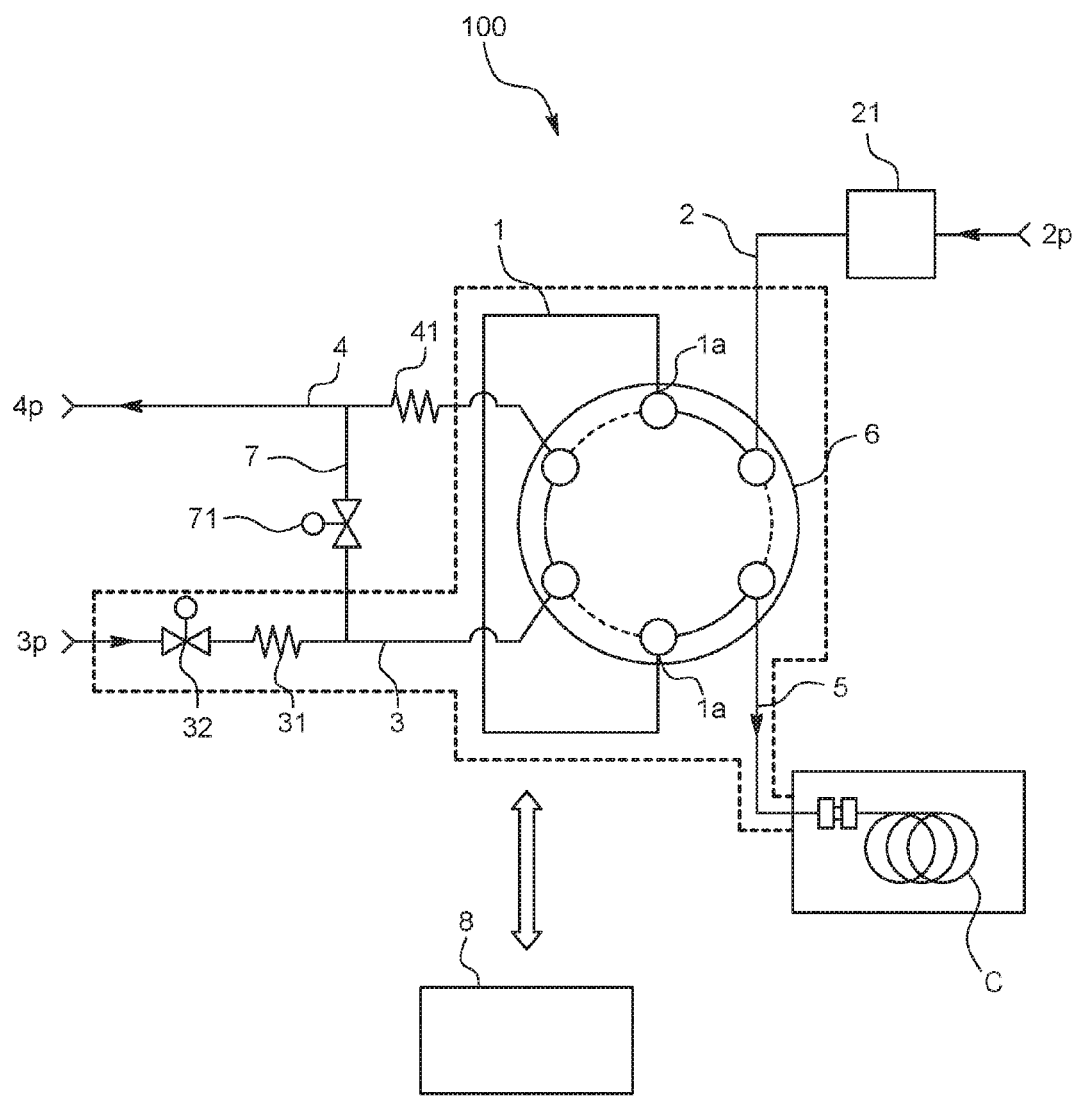
FIG. 4 is a fluid circuit diagram illustrating the configuration of a sampler in one embodiment of the present invention.

A sampler 100 according to the present embodiment is one that as illustrated in FIG. 4, supplies a constant volume of sample gas to a column C of a chromatograph arranged to analyze the sample gas, and includes: a constant volume tube 1, carrier introduction line 2, sample introduction line 3, sample discharge line 4, and control mechanism 8. This configuration has been described as the conventional configuration, and therefore a detailed description thereof will be omitted.

Also, as illustrated in the same diagram, the sampler 100 in the present embodiment further includes: in addition to the control mechanism 8 adapted to automatically send out the sample gas, a bypass line 7 provided between the sample introduction line 3 and the sample discharge line 4 in parallel with the constant volume tube 1, an on-off valve 71 (hereinafter also referred to as a bypass valve 71) provided in the bypass line 7, and a fluid resistive member 41 provided in the sample discharge line 4.

The control mechanism 8 is an electric circuit including a CPU, memory, communication port, driver, and the like, and one that outputs control signals to a carrier flow rate control device 21 provided in the carrier introduction line 2, a multiport valve 6, a bypass valve 71, and the like, and controls them in a predetermined sequence to send out the sample gas to the column C.

The bypass line 7 is one formed of a tubular member having a smaller fluid resistance than that of the constant volume tube 1.

The bypass valve 71 is a solenoid valve, and controlled to open/close by the control mechanism 8. The bypass valve 71 may be, besides the solenoid valve, a remote valve such as a pneumatic valve.

The fluid resistive member 41 is one formed of a capillary or an orifice, and the fluid resistance thereof is set to be larger than that of the constant volume tube 1.

Note that in FIG. 4, an area surrounded by a dashed line is kept at a constant temperature by an unillustrated temperature controller such as a heater.

Next, the action of the sampler 100 will be described.

Before the start of measurement (in an initial state), an on-off valve 32 (hereinafter also referred to as a sample introduction valve 32) provided in the start point part of the sample introduction line 3 is closed, and the sample gas is not introduced into the sample introduction line 3. Also, the carrier flow rate control device 21 is closed, and the carrier gas is not introduced into the carrier introduction line 2.

When an operator indicates the start of the measurement using an unillustrated input means (such as a switch, mouse, and keyboard) in this state, the control mechanism 8 receives the resulting signal and the action is started.

First, the control mechanism 8 sets the multiport valve 6 to the first mode, as well as closing the bypass valve 71.

Then, the control mechanism 8 opens the sample introduction valve 32 to flow the sample gas into the sample introduction line 3, as well as controlling the carrier flow rate control device 21 to circulate the carrier gas having a constant flow rate through the carrier introduction line 2.

Figure 5:
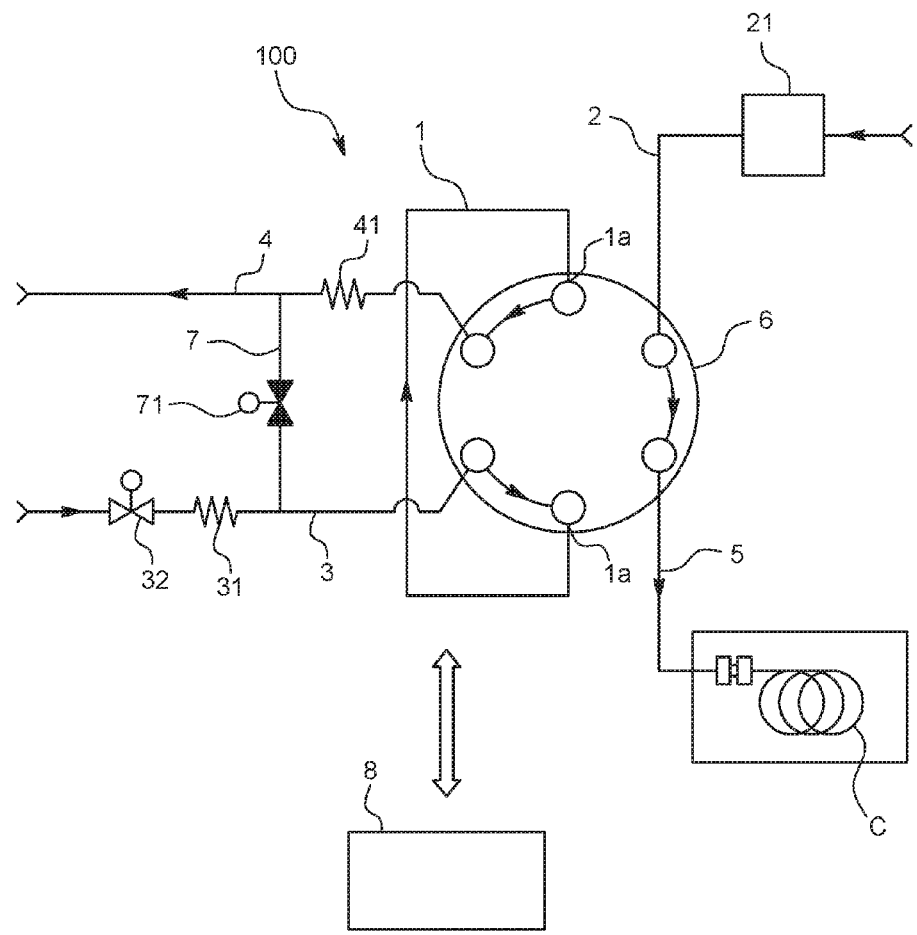
FIG. 5 is a fluid circuit diagram illustrating an action state of the sampler in the first half of a first mode in the same embodiment.

In doing so, as illustrated in FIG. 5, the sample gas flows from the sample supply source into the sample introduction line 3, passes through the constant volume tube 1, and is discharged from the sample discharge line 4. The sample gas does not flow through the bypass line 7. On the other hand, the carrier gas is introduced into the column C to purge the inside of the column C.

Figure 6:
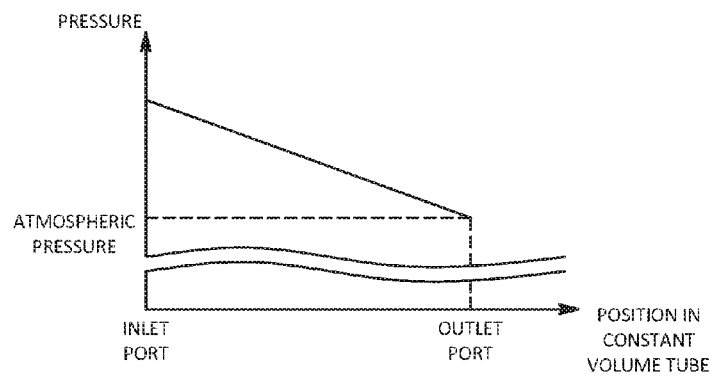
FIG. 6 is a graph illustrating pressure inside a constant volume tube in the state of FIG. 5.

The control mechanism 8 keeps this state for at least a predetermined period, i.e., for a period necessary to purge residual gas inside the constant volume tube 1 with the sample gas and fill the inside of the constant volume tube 1 with the sample gas. In this state, as illustrated in FIG. 6, a large pressure depending on the pressure of the sample supply source acts on the inlet port of the constant volume tube 1, and inside the constant volume tube 1, a large pressure gradient is generated.

Figure 7:
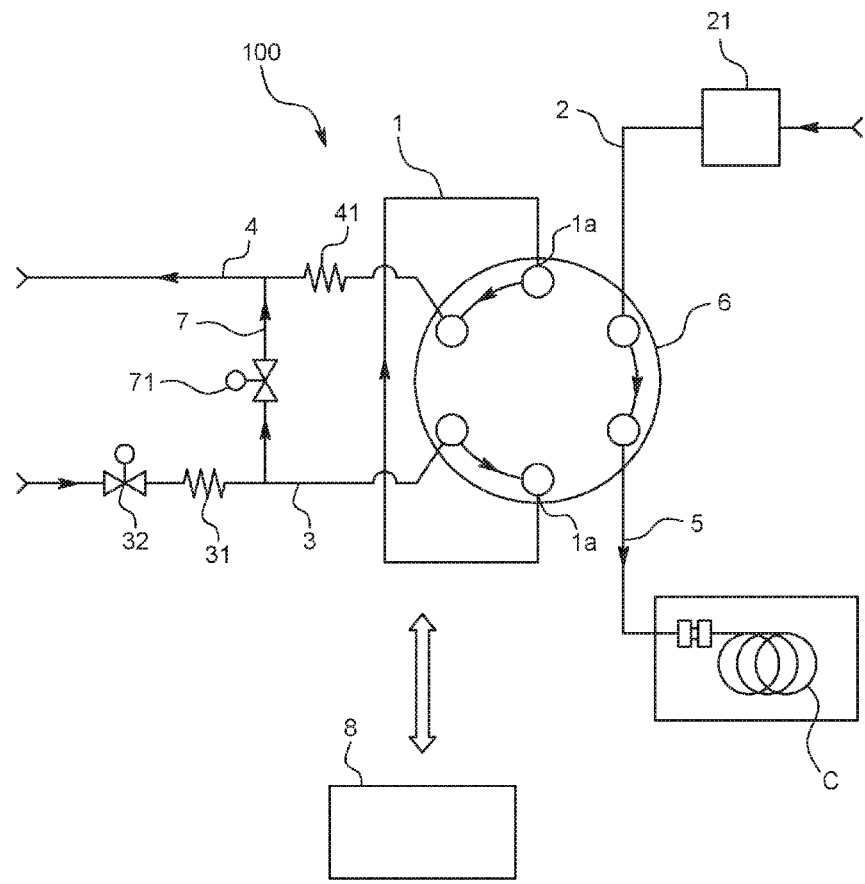
FIG. 7 is a fluid circuit diagram illustrating an action state of the sampler in the second half of the first mode in the same embodiment.

Subsequently, the control mechanism 8 opens the bypass valve 71. In doing so, as illustrated in FIG. 7, a large portion of the sample gas flows through the bypass line 7.

Figure 8:
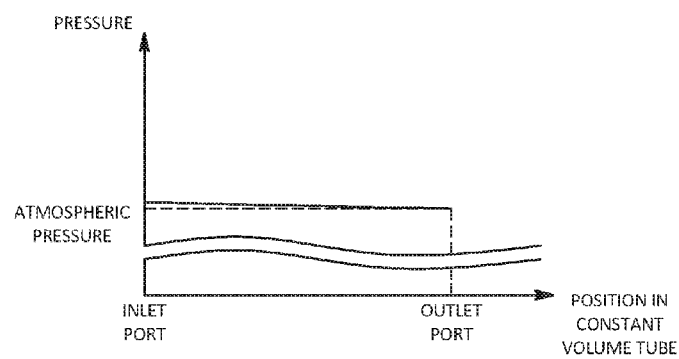
FIG. 8 is a graph illustrating the pressure inside the constant volume tube in the state of FIG. 7.

Since the bypass valve 71 has very small fluid resistance, the pressure difference between the inlet and outlet ports of the bypass valve 71 hardly occurs, and the pressure inside the bypass valve is kept substantially at atmospheric pressure. As a result, as illustrated in FIG. 8, the inlet and outlet pressures of the constant volume tube 1 arranged in parallel with the bypass line 7 also decrease to substantially atmospheric pressure although the inlet pressure is slightly higher, and correspondingly, the pressure of the sample gas inside the constant volume tube 1 is regulated substantially to atmospheric pressure.

Figure 9:
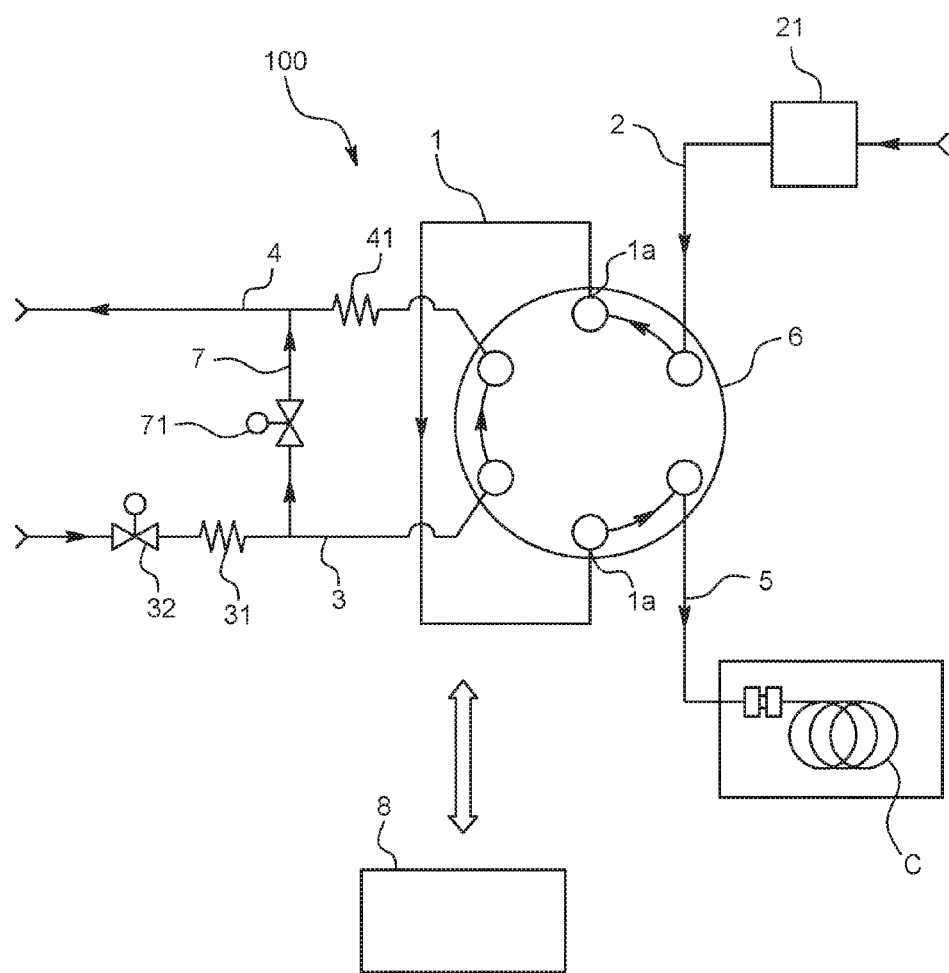
FIG. 9 is a fluid circuit diagram illustrating an action state of the sampler in a second mode in the same embodiment.

After that, as illustrated in FIG. 9, the control mechanism 8 switches the multiport valve 6 to a second mode in a state of opening the sample introduction valve 32 and the bypass valve 71. In doing so, the sample gas filled in the constant volume tube 1 is pushed out by the carrier gas and sent out to the column C. In addition, after switching the multiport valve 6 to the second mode, the control mechanism 8 closes the sample introduction valve 32 at appropriate timing.

The above-described configuration makes it possible to, only by adding a very simple structure, i.e., providing the bypass line 7 mainly, even when the pressure of the sample supply source varies at every time of measurement, suppress the resulting variation in sample gas pressure inside the constant volume tube 1 and keep the sample gas pressure substantially at a constant pressure (atmospheric pressure).

As a result, since the temperature of the constant volume of the sample gas inside the constant volume tube 1 is also kept constant by the temperature controller, when the pressure is kept constant, the gas state equation ($pV=nRT$) gives a constant mass (or a molar number).

Accordingly, for example, even when the same type of sample gas is measured multiple times, the sample gas having a mass that is the same as much as possible at every time of measurement is sent out to the column C, and consequently the reproducibility of measurement can be improved.

Note that the present invention is not limited to the above-described embodiment.

For example, the bypass valve 71 does not have to be necessarily provided. However, as compared with the above-described embodiment, a large portion of the sample gas flows through the bypass line 7 from the beginning of the first mode, and thereby the flow rate of the sample gas flowing through the constant volume tube 1 is decreased, thus causing the disadvantage of requiring a long time for filling the sample gas in the constant volume tube 1.

The fluid resistive member 41 provided in the sample discharge line 4 is not necessarily required. However, the presence of the fluid resistive member 41 provides the effects of being able to prevent the sample gas from flowing back from the bypass line 7 and, not having to decrease the fluid resistance of the bypass line 7 more than necessary, i.e., not having to increase the diameter of the bypass line 7.

Figure 10:
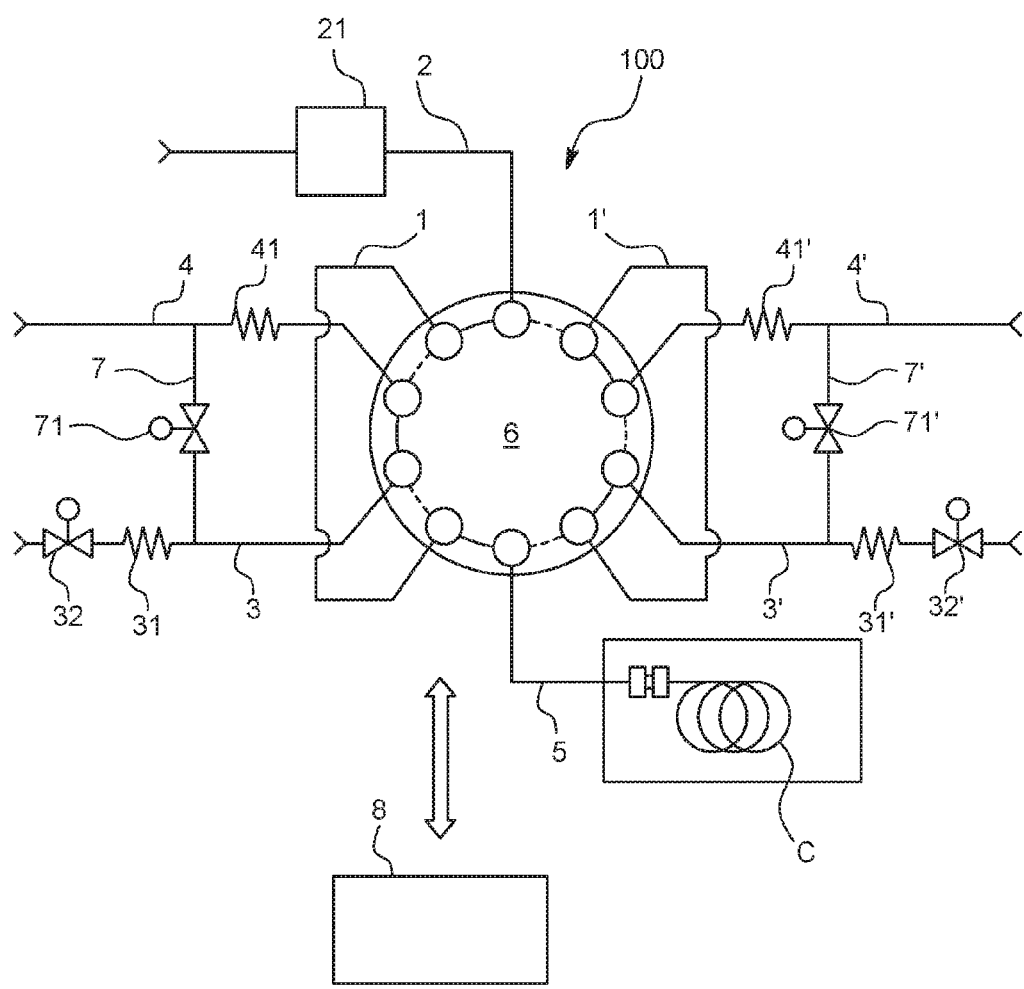
FIG. 10 is a fluid circuit diagram illustrating the configuration of a sampler in another embodiment of the present invention.

As illustrated in FIG. 10, the sampler 100 may be configured to be able to alternately introduce reference gas and the sample gas into the column C.

Describing this specifically, in the configuration of the above-described embodiment, the multiport valve 6 is replaced by a 10-port valve, and a fluid circuit for sending out the constant volume of the reference gas to the column C is provided symmetrically, in terms of a circuit, to the fluid circuit for sending out the constant volume of the sample gas to the column C In FIG. 10, numeral 1' represents a second constant volume tube, numeral 3' a reference introduction line, numeral 31' a second flow rate limiting member, numeral 32' a reference introduction valve, numeral 4' a reference discharge line, numeral 41' a second fluid resistive member, numeral 7' a second bypass line, and numeral 71' a second bypass valve.

Next, the action of the sampler 100 will be described.

Figure 11:
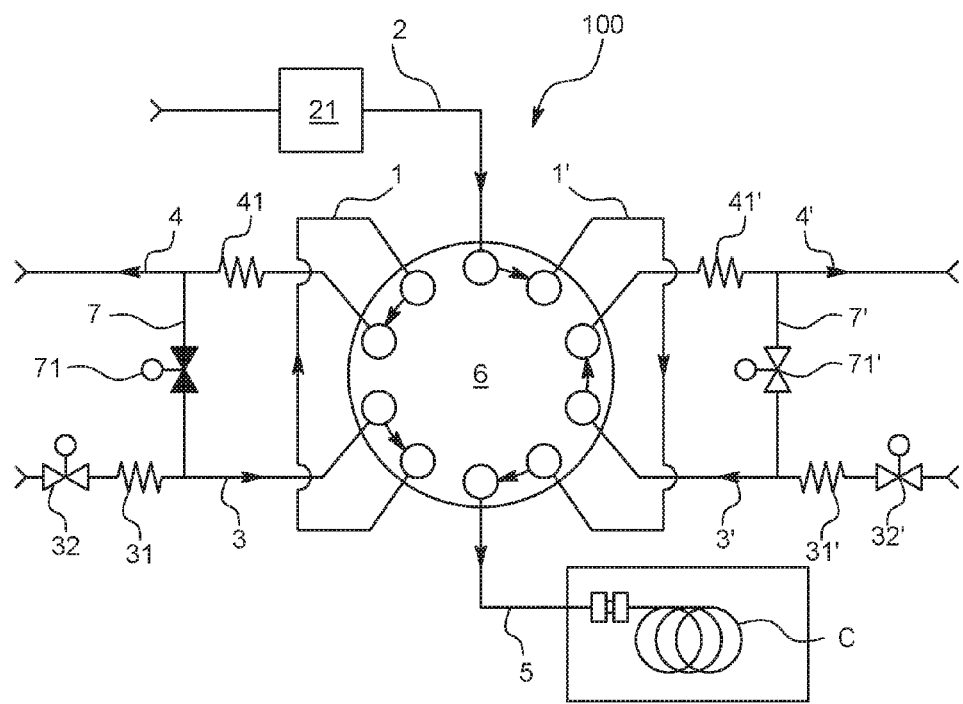
FIG. 11 is a fluid circuit diagram illustrating an action state of the sampler in the same embodiment.
Figure 12:
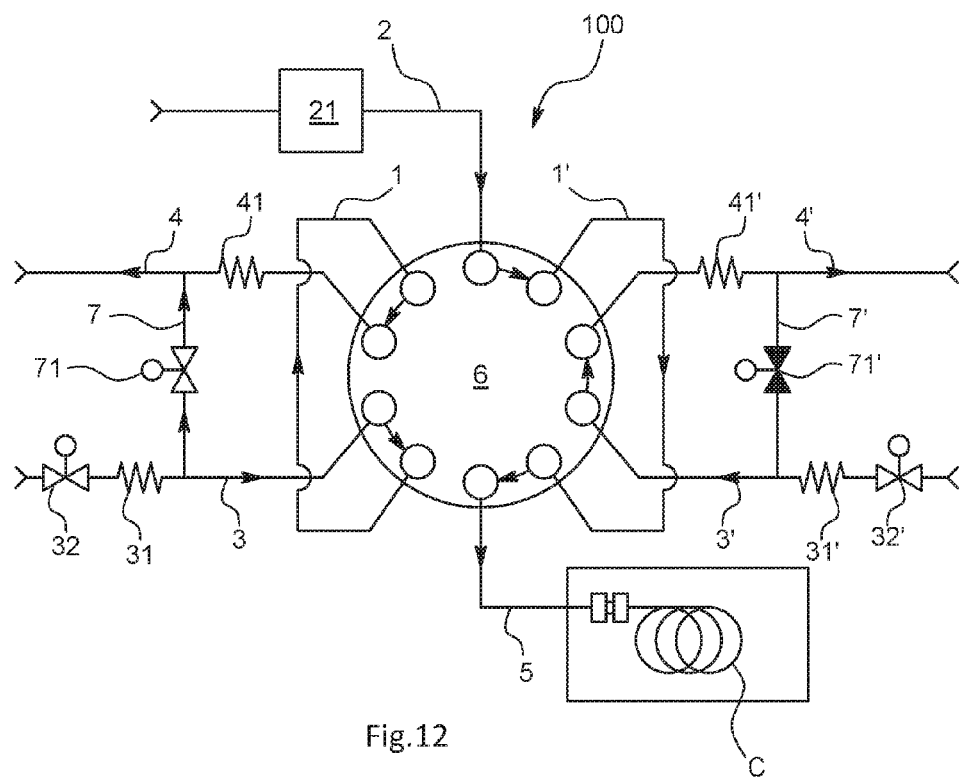
FIG. 12 is a fluid circuit diagram illustrating an action state of the sampler in the same embodiment.

The multiport valve 6 is switchable between a first mode and a second mode, and the flow of the sample gas in each of the modes is the same as that in the above-described embodiment. That is, in the first mode, a state of FIG. 11 is transitioned to a state of FIG. 12, in which the sample gas is filled in the constant volume tube 1 at a constant pressure (atmospheric pressure), and then the first mode is switched to the second mode illustrated in FIG. 13, in which the sample gas is sent out to the column.

Figure 13:
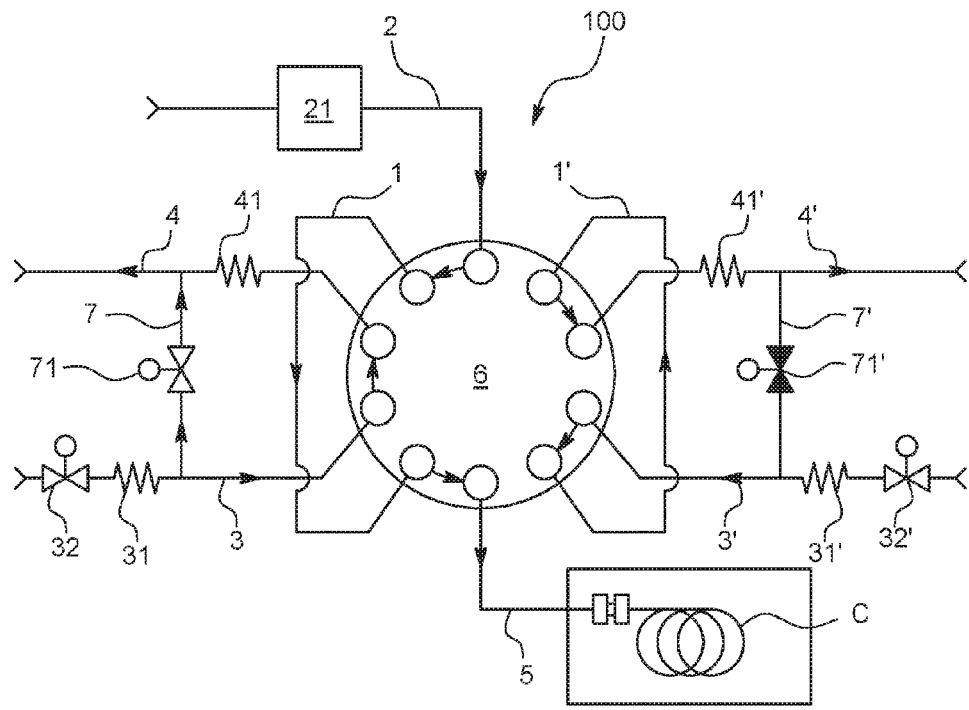
FIG. 13 is a fluid circuit diagram illustrating an action state of the sampler in the same embodiment.
Figure 14:
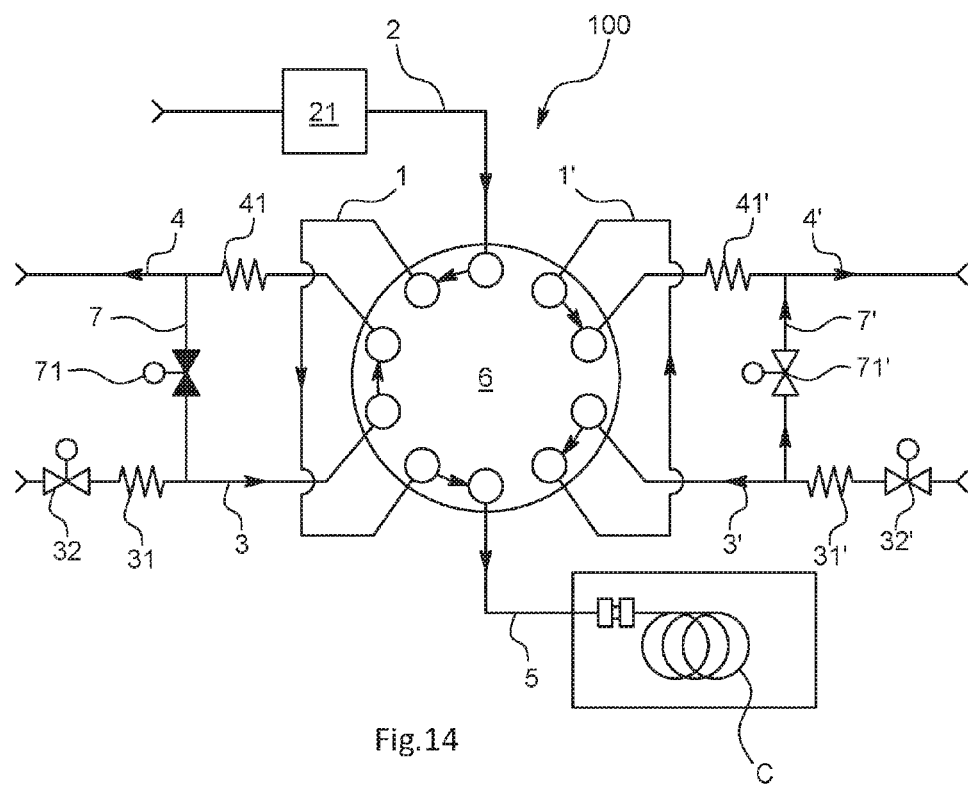
FIG. 14 is a fluid circuit diagram illustrating an action state of the sampler in the same embodiment.

On the other hand, in the second mode in which the sample gas is sent out to the column C (FIG. 13), the reference gas is filled in the second constant volume tube 1'. Subsequently, while keeping the second mode, a state of FIG. 13 is transitioned to a state illustrated in FIG. 14 in which the second bypass valve 71' is opened, and the pressure inside the second constant volume tube 1' is regulated to a constant pressure (atmospheric pressure). After that, the multiport valve 6 is switched to the first mode illustrated in FIG. 11, and the reference gas in the second constant volume tube 1' is sent out to the column C.

The control mechanism 8 is not necessarily required, and an operator may operate the respective valves in an equivalent sequence to introduce the sample gas and the reference gas into the column C.

In addition, when attempting to quantitatively analyze the reference gas and the sample gas having higher concentration than the reference gas with both gases having the same volume, a peak of the sample gas becomes too high relative to that of the reference gas, and this causes the problem of increasing an analysis error. For this reason, when in the sampler in the embodiment illustrated in FIG. 10, weighing the reference gas using the second constant volume tube 1' and weighing the sample gas having higher concentration than the reference gas using the first constant volume tube 1, it is configured to make the volume of the second constant volume tube 1' larger than that of the first constant volume tube 1, and make the ratio of the volume of the first constant volume tube 1 to that of the second constant volume tube 1' equal to the ratio of the concentration of the reference gas to that of the sample gas. Such a configuration makes it possible for a peak obtained by analyzing the reference gas weighed using the second constant volume tube 1' and a peak obtained by analyzing the sample gas weighed using the first constant volume tube 1 to have almost the same height, and therefore an analysis error can be decreased.

Figure 17:
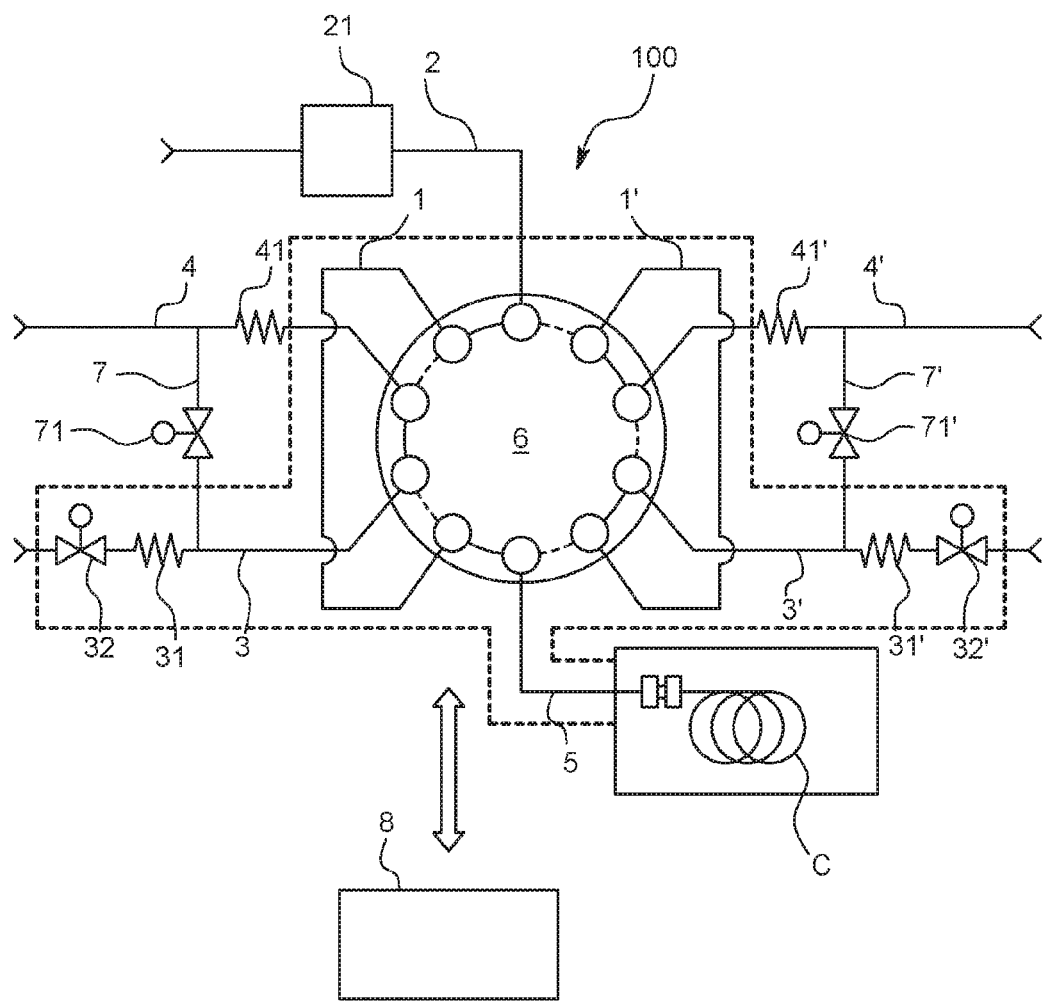
FIG. 17 is a fluid circuit diagram illustrating the configuration of a sampler in still yet another embodiment of the present invention.

Further, in order to prevent the sample and/or the like from being attached into respective lines and respective devices provided in the lines, a part surrounded by a dashed line in FIG. 17, specifically, constant volume tubes 1 and 1', sample introduction line 3, reference introduction line 3', flow rate control members 31 and 31', sample introduction valve 32, reference introduction valve 32', a column communicating line 5, and a line switching mechanism 6 may be provided with a heating mechanism such as a heater. In addition, the heating mechanism may include a temperature control function.

In order to regulate the pressure inside the constant volume tube to the constant pressure, the above-described embodiment uses the bypass line 7, but may use a constant pressure mechanism such as a pressure regulation valve.

Figure 15:
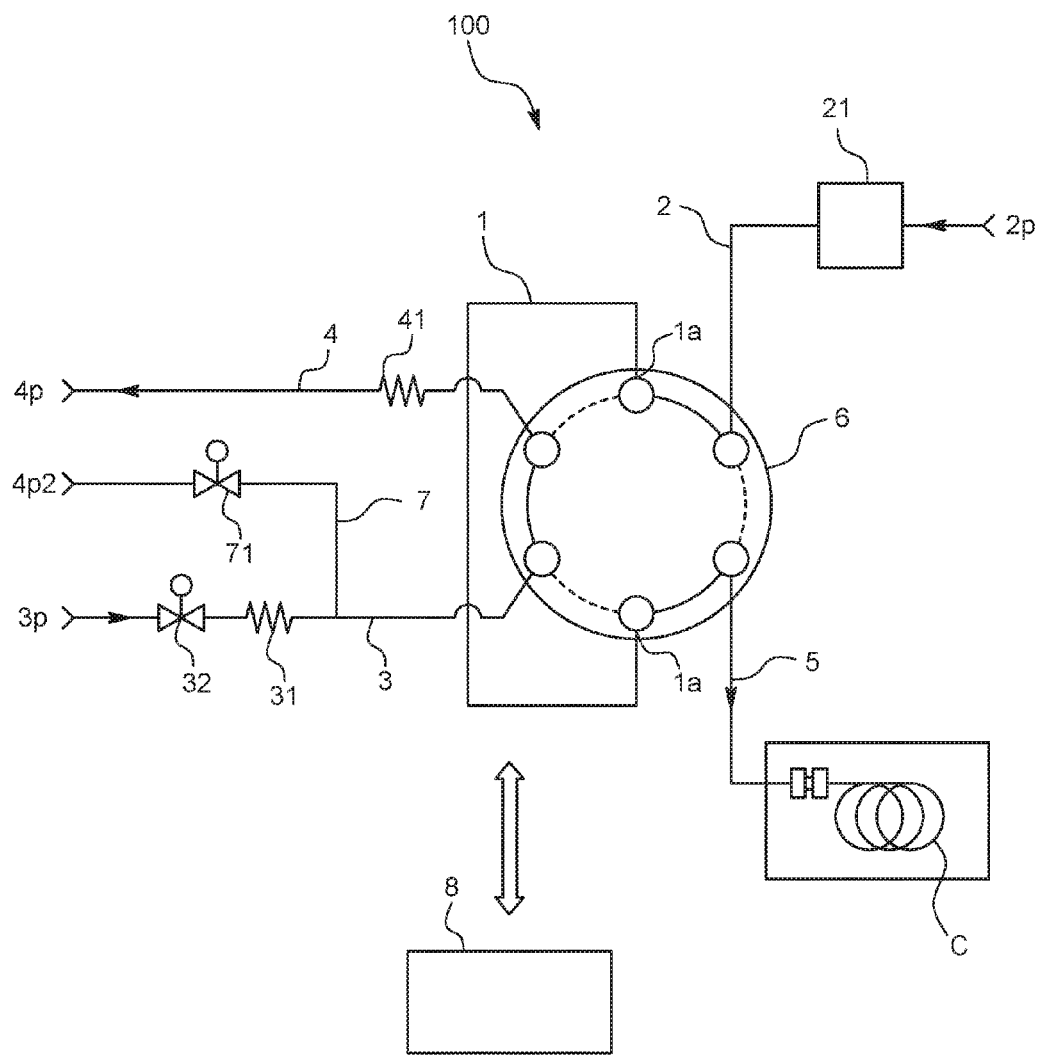
FIG. 15 is a fluid circuit diagram illustrating the configuration of a sampler in still another embodiment of the present invention.

In the above-described embodiment, the other end of the bypass line 7 is connected to the sample discharge line 4. However, as illustrated in FIG. 15, it may be adapted not to directly connect the other end of the bypass line to the sample discharge line 4 but to connect the other end of the bypass line to a second discharge port 4p2 communicatively connecting to the discharge space. That is, this is a configuration in which the other end of the bypass line 7 is connected to the sample discharge line 4 through the discharge space. However, in the case of this variation, the flow rate of the sample gas flowing through the discharge port 4p decreases, thus causing the disadvantage that the air (oxygen) permeates from the discharge space side into the constant volume tube 1. On the other hand, in the above-described embodiment, there is the only one discharge port 4p, and the flow rate of the sample gas flowing out of the discharge port 4p is large, so that the above problem can be prevented.

Further, a discharge space communicatively connected with the second discharge port 4p2, and a discharge space communicatively connected with the discharge port 4p may be separately prepared. In this case, it is preferable to keep the respective discharge spaces at the same pressure, and in doing so, the pressure inside the constant volume tube can be regulated to a constant pressure.

Also, the above-described embodiment has the configuration in which the supply source of the sample fluid is a gas cylinder or the like, and at inconstant pressure, and the discharge space is at the constant pressure such as atmospheric pressure. In addition, in the first mode, the pressure inside the constant volume tube 1 is made constant as a result of matching the pressure of the discharge space.

Meanwhile, in cases such as when atmospheric components are analyzed, the sample supply source is atmospheric space and therefore at a constant pressure, and the discharge space is a space at inconstant pressure as a result of being brought to negative pressure by a suction pump or the like.

Figure 16:
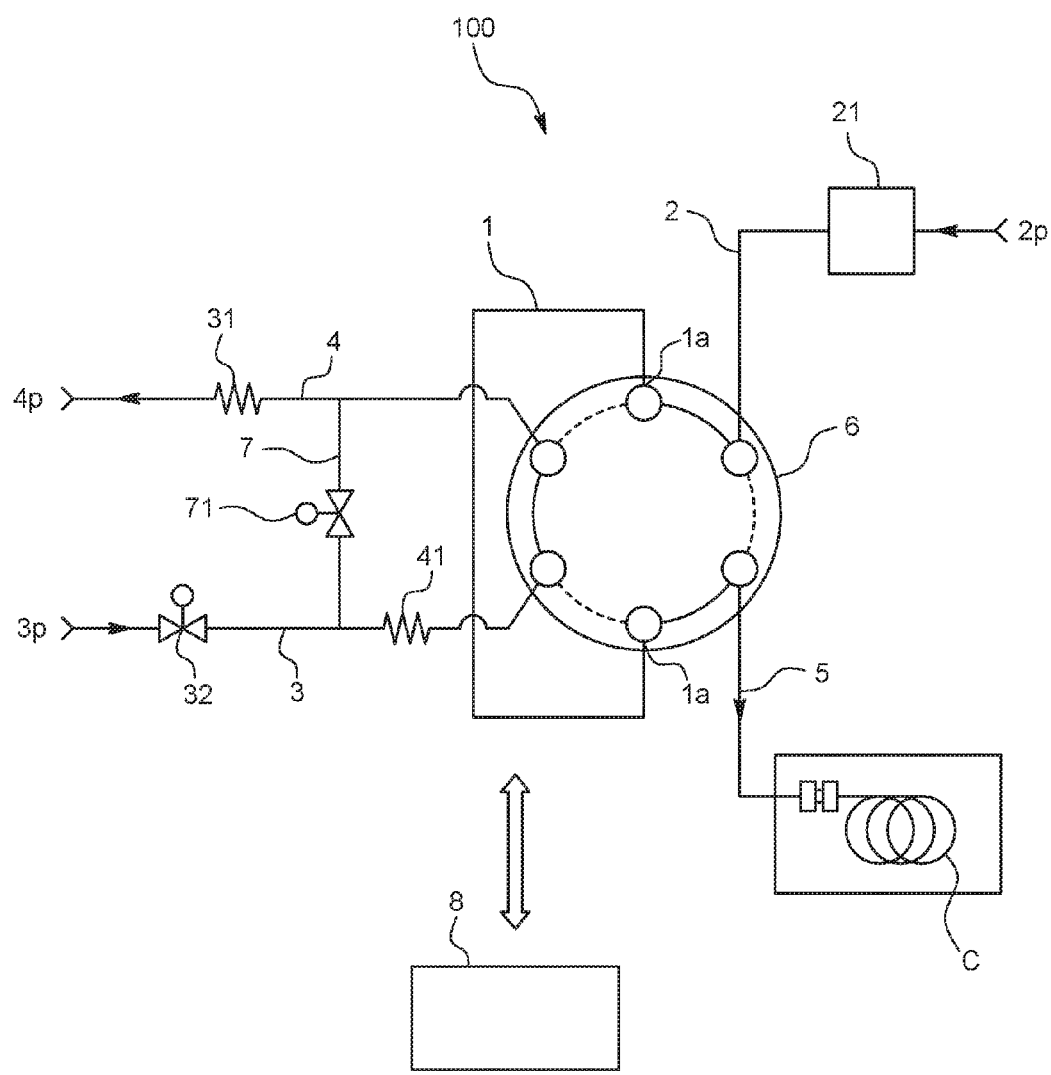
FIG. 16 is a fluid circuit diagram illustrating the configuration of a sampler in yet another embodiment of the present invention.

In such a case, as illustrated in FIG. 16, a flow rate limiting member 31 is provided in the sample discharge line 4. Accordingly, in the first mode, the pressure inside the constant volume tube 1 is made constant as a result of matching the pressure of the supply source. In addition, the fluid resistive member 41 is provided in the sample introduction line 3.

In the second mode, the sample fluid contained in the constant volume tube may be introduced into the column by bringing the column to negative pressure, or by bringing the carrier introduction line to positive pressure.

Besides, it goes without saying that the present invention can be variously modified without departing the scope thereof.

REFERENCE SIGNS LIST

100: Chromatograph sampler
1: Constant volume tube
1a: Fluid inlet/outlet port
2: Carrier introduction line
3: Sample introduction line
31: Flow rate limiting member
4: Sample discharge line
41: Fluid resistive member
6: Line switching mechanism (multiport valve)
7: Bypass line
71: On-off valve (bypass valve)
8: Control mechanism

The invention claimed is:

1. A chromatograph sampler configured to supply a sample fluid as a measurement target to a column of a chromatograph, the chromatograph sampler comprising:
a constant volume tube having a pair of fluid inlet/outlet ports;
a sample introduction line into which the sample fluid is introduced from a supply source of the sample fluid;
a sample discharge line from which the sample fluid is discharged to a discharge space for the sample fluid;
a multiport valve configured to switch between a first mode in which any one of the fluid inlet/outlet ports of the constant volume tube is connected to the sample introduction line, the other is connected to the sample discharge line, and the sample fluid is filled in the constant volume tube while circulating, and a second mode in which both of the fluid inlet/outlet ports are respectively disconnected from the sample introduction line and the sample discharge line and any one of the fluid inlet/outlet ports is connected to the column;
a controller configured to keep the multiport valve in the first mode to fill the sample fluid in the constant volume tube, and then switch the multiport valve to the second mode to introduce the sample fluid in the constant volume tube into the column; and
a bypass line of which one end is connected to the sample introduction line and the other end is connected to the sample discharge line; and
the chromatograph sampler is configured to switch between a state where the sample fluid flows only through the constant volume tube, and a state where the sample fluid flows through both the constant volume tube and the bypass line in parallel.

2. The chromatograph sampler according to claim 1, configured such that:
the multiport valve is one that in the second mode, connects any one of the fluid inlet/outlet ports of the constant volume tube to a carrier introduction line into which a carrier fluid for transferring the sample fluid is introduced, and connects the other to the column; and
in the second mode, the sample fluid in the constant volume tube is pushed out by the carrier fluid and introduced into the column.

3. The chromatograph sampler according to claim 1, further comprising
an on-off valve provided in the bypass line,
the chromatograph sampler being configured to, in the first mode, flow the sample fluid through the constant volume tube in a state of closing the on-off valve to block the bypass line, and then open the on-off valve to also flow the sample fluid through the bypass line.

4. The chromatograph sampler according to claim 1, when the discharge space is at a constant pressure, further comprising
a flow rate limiter provided in the sample introduction line and on an upper stream side than the constant volume tube and the bypass line.

5. The chromatograph sampler according to claim 1, further comprising
a fluid resistive member connected to the constant volume tube in series.

6. A method for operating a chromatograph sampler comprising:
a constant volume tube having a pair of fluid inlet/outlet ports;
a sample introduction line into which a sample fluid as a measurement target is introduced from a supply source of the sample fluid;
a sample discharge line from which the sample fluid is discharged to a discharge space for the sample fluid; and
a bypass line of which one end is connected to the sample introduction line and the other end is connected to the sample discharge line, the method:
connecting any one of the fluid inlet/outlet ports of the constant volume tube to the sample introduction line and connecting the other to the sample discharge line to thereby flow the sample fluid through the constant volume tube and through the bypass line in parallel; then
disconnecting both of the fluid inlet/outlet ports of the constant volume tube respectively from the sample introduction line and the sample discharge line; and
connecting any one of the fluid inlet/outlet ports to a column of a chromatograph to introduce the sample fluid in the constant volume tube into the column.

7. The method for operating a chromatograph sampler according to claim 6, the method:
disconnecting both of the fluid inlet/outlet ports of the constant volume tube respectively from the sample introduction line and the sample discharge line; then
connecting any one of the fluid inlet/outlet ports to a carrier introduction line into which a carrier fluid for transferring the sample fluid is introduced, and connecting the other to the column; and
pushing out the sample fluid in the constant volume tube by the carrier fluid to introduce the sample fluid into the column.

8. A chromatograph sampler configured to supply a sample fluid as a measurement target to a column of a chromatograph, the chromatograph sampler comprising:

a constant volume tube having a pair of fluid inlet/outlet ports;

a sample introduction line into which the sample fluid is introduced from a supply source of the sample fluid;

a sample discharge line from which the sample fluid is discharged to a discharge space for the sample fluid;

a multiport valve configured to switch between a first mode in which any one of the fluid inlet/outlet ports of the constant volume tube is connected to the sample introduction line, the other is connected to the sample discharge line, and the sample fluid is filled in the constant volume tube while circulating, and a second mode in which both of the fluid inlet/outlet ports of the constant volume tube are respectively disconnected from the sample introduction line and the sample discharge line and any one of the fluid inlet/outlet ports is connected to the column;

a controller configured to keep the multiport valve in the first mode to fill the sample fluid in the constant volume tube, and then switch the multiport valve to the second mode to introduce the sample fluid in the constant volume tube into the column; and a bypass line configured to at least immediately before switching from the first mode to the second mode, keep pressure of the constant volume tube at a predetermined value; and the chromatograph sampler is configured to switch between a state where the sample fluid flows only through the constant volume tube, and a state where the sample fluid flows through both the constant volume tube and the bypass line in parallel.

* * * * *